(12) United States Patent  
Sato et al.

(10) Patent No.: US 7,651,470 B2  
(45) Date of Patent: Jan. 26, 2010

(54) SWALLOWING FUNCTION EVALUATING APPARATUS

(75) Inventors: Junya Sato, Yokohamai (JP); Masato Nakajima, Yokohama (JP); Yasuhiro Takemura, Tokyo (JP)

(73) Assignees: Sumitomo Osaka Cement Co., Ltd., Tokyo (JP); Keio University, Tokyo (JP)

( * ) Notice: Subject to any disclaimer, the term of this patent is extended or adjusted under 35 U.S.C. 154(b) by 0 days.

(21) Appl. No.: 11/727,654

(22) Filed: Mar. 27, 2007

(65) Prior Publication Data

US 2007/0238920 A1    Oct. 11, 2007

(30) Foreign Application Priority Data

Mar. 29, 2006    (JP)    ............................. 2006-092093

(51) Int. Cl.  
*A61B 1/00*    (2006.01)
(52) U.S. Cl. .................. 600/587; 600/593; 600/595
(58) Field of Classification Search .......... 600/587, 600/593, 595  
See application file for complete search history.

(56) References Cited

U.S. PATENT DOCUMENTS

| | | | | |
|---|---|---|---|---|
| 4,657,394 | A | * | 4/1987 | Halioua ...................... 356/604 |
| 5,986,770 | A | * | 11/1999 | Hein et al. ................... 356/446 |
| 2003/0007159 | A1 | * | 1/2003 | Franke et al. ............... 356/604 |
| 2004/0082874 | A1 | * | 4/2004 | Aoki et al. .................. 600/534 |
| 2004/0210155 | A1 | * | 10/2004 | Takemura et al. ........... 600/534 |
| 2006/0097422 | A1 | * | 5/2006 | Diamond ..................... 264/222 |
| 2006/0279428 | A1 | | 12/2006 | Sato et al. |

FOREIGN PATENT DOCUMENTS

| | | | |
|---|---|---|---|
| EP | 1787582 | * | 5/2007 |
| JP | 2002-175582 A | | 6/2002 |
| JP | 2005-003366 | | 1/2005 |
| JP | 2005-245974 | | 9/2005 |
| WO | WO 2006013797 | * | 2/2006 |

OTHER PUBLICATIONS

The Ingestion and Swallow Rehabilitation Society of Japan, "The Japanese Journal of Dysphagia Rehabilitation", vol. 8, No. 1, pp. 71-86, 2004.

* cited by examiner

*Primary Examiner*—Max Hindenburg  
*Assistant Examiner*—Michael C Stout  
(74) *Attorney, Agent, or Firm*—Foley & Lardner LLP

(57) ABSTRACT

A swallowing function evaluating apparatus capable of quantitatively evaluating a swallowing function safely and repeatedly, which comprises a height variation detecting unit 10 for detecting a variation in the height of the surface of a throat from a predetermined reference position in the height direction in which a thyroid protrudes and an analyzing unit 21 for time-serially analyzing the variation to calculate an index for evaluating a swallowing function. The swallowing function evaluating apparatus can repeatedly detect the variation safely without radiating X-rays and can quantitatively evaluate the swallowing function using a calculated index.

15 Claims, 13 Drawing Sheets

SWALLOWING FUNCTION EVALUATING APPARATUS

BACKGROUND OF THE INVENTION

1. Technical Field

The present invention relates to a swallowing function evaluating apparatus, and in particular a swallowing function evaluating apparatus capable of quantitatively evaluating a swallowing function safely and repeatedly.

2. Related Art

In recent years, a swallowing disorder appearing in a patient suffering from muscular dystrophy or myasthenia has also attracted considerable attention as a disease caused by weak muscular strength due to aging. This suggests that the next aging society will cause patients suffering from the swallowing disorder to increase. In general, for example, a video fluorography (VF (Video Fluorography)) examination for swallowing, a method of examining the movement of a throat by touch, or a drink test is used to diagnose the swallowing disorder.

In the video fluorography (VF) examination for swallowing, the swallowing disorder of an examinee is diagnosed by letting the examinee drink liquid containing a contrast medium and continuously radiating X-rays onto the front and side of the throat of the examinee to capture the image of the swallowing motion of the examinee (for example, see Non-Patent Document 1). This method enables to see the image of the inside of the larynx and thus improve the accuracy of diagnosis. In the examination by touch, needless to say, the doctor touches a patient on body by hand and diagnoses the disease. The drink test is a diagnostic method of letting an examinee drink water and observing the swallowing motion with naked eyes at the time from the outside. The examination by touch and the drink test can be easily performed. A monitoring apparatus has been used to detect the displacement of the body of a sleeping examinee in the height direction (the displacement of the abdomen), not the movement of the throat, and the monitoring apparatus includes an illumination pattern emitting unit that emits a predetermined illumination pattern (bright spot) to the sleeping examinee, an image capturing device that continuously captures the image of the light with wave length emitted, and a shift calculating unit that calculates the shift of the illumination pattern between two frames of images captured by the image capturing device at different times (for example, see Patent Document 1).

[Patent Document 1] JP-A-2002-175582

[Non-Patent Document 1] 'The Japanese Journal of Dysphagia Rehabilitation', Volume 8, Number 1, pp. 71-86, 2004

However, in the video fluorography (VF) examination, X-rays are continuously radiated to a body of the examinee to be examined, and thus it is necessary to pay special attention to exposure to radiation, and it is not allowed to repeatedly perform the video fluorography (VF) examination on the same person. On the other hand, in the examination by touch and the drink test, since diagnosis is mainly performed by examining the appearance of the examinee, the diagnosis result generally depends on the subjectivity of the doctor, which makes it difficult to get quantitative evaluation.

The invention has been made to solve the above-mentioned problems, and it is an object of the invention to provide a swallowing function evaluating apparatus capable of quantitatively evaluating a swallowing function safely and repeatedly.

SUMMARY OF THE INVENTION

In order to achieve the object, according to the aspect (1) of the invention, referring to FIGS. 1 and 2 e.g., a swallowing function evaluating apparatus comprises a height variation detecting unit 10 for detecting a variation in a height of a position of a surface of a throat St from a predetermined reference position in a height direction H in which a thyroid Sc protrudes; and an analyzing unit 21 for time-serially analyzing the variation to calculate an index for evaluating a swallowing function.

According to the above-mentioned structure, since the swallowing function evaluating apparatus comprises the height variation detecting unit for detecting a variation in a height of a position of the surface of the throat from a predetermined reference position in the height direction in which the thyroid protrudes, it can safely and repeatedly detect the height variation without radiating X-rays. In addition, since the swallowing function evaluating apparatus comprises the analyzing unit that calculate an index for evaluating the swallowing function, it can quantitatively evaluate the swallowing function on the basis of the calculated index.

According to aspect (2) of the invention, in the swallowing function evaluating apparatus according to the aspect (1), referring to FIGS. 1 and 2, preferably, the height variation detecting unit 10 is configured to detect the variations at a plurality of points in a thyroid moving direction P in which the thyroid Sc moves during a swallowing motion and a widthwise direction B that is orthogonal to both the thyroid moving direction P and the height direction H, and the analyzing unit 21 is configured to calculate a movement distance of the thyroid Sc in the thyroid moving direction P during the swallowing motion on the basis of the variation. For example, the movement distance of the thyroid Sc is calculated by tracing a point that protrudes furthest in the height direction H.

According to the above-mentioned structure, the movement distance of the thyroid Sc in the thyroid moving direction P during the swallowing motion is calculated on the basis of the variation, which makes it possible to quantitatively evaluate the swallowing function using the movement distance of the thyroid as an evaluation value.

According to aspect (3) of the invention, in the swallowing function evaluating apparatus according to aspect (1), referring to FIGS. 1 and 2 e.g., preferably, the analyzing unit 21 adds up across along the widthwise direction the variations in the height of each row of points, the rows being arranged with a predetermined interval in the thyroid moving direction on the surface of the thyroid Sc at a point of time of the time series, and calculates the movement distance of the thyroid Sc using a position where the added value is the maximum in the thyroid moving direction P or a position Gu (for example, see FIG. 11) indicating the bias of the added value in the thyroid moving direction P as the position of the thyroid Sc.

According to the above-mentioned structure, the movement distance of the thyroid is calculated by using a position where the added value is the maximum in the thyroid moving direction or a position indicating the bias of the added value in the thyroid moving direction as the position of the thyroid. Therefore, the structure makes it possible to decrease the possibility that the position of the thyroid will be erroneously calculated due to noise and thus to stably evaluate the swallowing function, as compared to the structure in which simply a position where the maximum variation is obtained is used as the position of the thyroid.

According to aspect (4) of the invention, in the swallowing function evaluating apparatus according to aspect (1), referring to FIGS. 1 and 2, preferably, the height variation detecting unit 10 is configured to detect the variations at a plurality of points in a thyroid moving direction P in which the thyroid Sc moves during a swallowing motion and a widthwise direction B that is orthogonal to both the thyroid moving direction P and the height direction H, and the analyzing unit 21 is configured to add up across along the widthwise direction the variations in the height of each row of points, the rows being arranged with a predetermined interval in the thyroid moving direction on the surface of the thyroid Sc at a point of time of the time series.

According to the above-mentioned structure, the analyzing unit is configured to add up across along the widthwise direction the variations in the height of each row of points, the rows being arranged with a predetermined interval in the thyroid moving direction on the surface of the thyroid at a point of time of the time series. Therefore, it is possible to process points for detecting a plurality of variations in the unit of a row of points and thus reduce the load of analysis. In addition, it is possible to obtain the distribution of height variations in the thyroid moving direction due to the movement of the thyroid.

According to aspect (5) of the invention, in the swallowing function evaluating apparatus according to aspect (4), as shown in FIGS. 1 and 11 e.g., preferably, the analyzing unit 21 separately adds up the variations in the direction Hu (for example, see FIG. 2) in which the thyroid Sc protrudes and in an opposite direction Hd (for example, see FIG. 2) thereto, and calculates at least one of a height direction component deviation distance Hb, which is the distance in the height direction H between positions Gu and Gd indicating the bias of the two sums of variations when the separately added up values are viewed in the thyroid moving direction P, and a thyroid moving direction component deviation distance Pb, which is the distance in the thyroid moving direction P between the positions Gu and Gd.

According to the above-mentioned structure, the variations are separately added up in the direction in which the thyroid protrudes and in the opposite direction thereto. Therefore, even when the position of the surface of the throat is changed from the predetermined reference position, it is possible to perform analysis without canceling the variations, in addition to the reduction in the load of analysis. The height direction component deviation distance can be used as a variation in the height direction, and the thyroid moving direction component deviation distance can be used as the moving speed of the thyroid when the concept of time is used. The two distances can be used as evaluation values.

According to aspect (6) of the invention, in the swallowing function evaluating apparatus according to aspect (5), referring to FIGS. 1 and 11 e.g., preferably, the analyzing unit 21 has at least one of functions of time-serially acquiring the height direction component deviation distance Hb during the swallowing motion and calculating the maximum value of the height direction component deviation distance Hb corresponding to the height direction component deviation distance Hb acquired during the swallowing motion, and time-serially acquiring the thyroid moving direction component deviation distance Pb during the swallowing motion and calculating the maximum value of the thyroid moving direction component deviation distance Pb corresponding to the thyroid moving direction component deviation distance Pb acquired during the swallowing motion.

According to the above-mentioned structure, at least one of the height direction component deviation distance and the thyroid moving direction component deviation distance is acquired, and a value that is the maximum at a point of time during swallowing motion is calculated. Therefore, the most remarkable value can be used as the object of evaluation, which makes it easy to evaluate the swallowing function.

According to aspect (7) of the invention, in the swallowing function evaluating apparatus according to aspect (4), referring to FIGS. 1 and 2, preferably, the analyzing unit 21 separately adds up the variations in the direction Hu in which the thyroid Sc protrudes and in the opposite direction Hd thereto, and further adds up the separately calculated sums in the thyroid moving direction P to time-serially calculate the total sum.

According to the above-mentioned structure, it is possible to evaluate all variations in the positions of the surface of the throat during the overall swallowing motion.

According to aspect (8) of the invention, as shown in FIG. 1 e.g., preferably, the swallowing function evaluating apparatus according to any one of aspect (1) to aspect (7) further comprises a swallowing function evaluating unit 22 for evaluating the swallowing function on the basis of the calculated index. The calculated index include, for example, the movement distance of the thyroid, the sum of variations, the height direction component deviation distance and the thyroid moving direction component deviation distance, and the maximum values of the height direction component deviation distance and the thyroid moving direction component deviation distance, and the total sum.

According to the above-mentioned structure, it is possible to quantitatively evaluate the swallowing function.

According to aspect (9) of the invention, as shown in FIG. 1 e.g., preferably, the swallowing function evaluating apparatus according to any one of aspect (1) to aspect (8) further comprises a display device 30 for visually displaying the calculated index.

According to the above-mentioned structure, it is possible to visually display the calculated index and thus easily apprehend the calculated index. As a result, it is possible to artificially evaluate the swallowing function on the basis of the calculated index.

According to aspect (10) of the invention, as shown in FIG. 8 e.g., in the swallowing function evaluating apparatus according to aspect (9), preferably, the display device is for displaying the calculated index to be visually displayed, in a convex or concave shape with respect to a cylindrical surface Fs as a tentative reference plane.

According to the above-mentioned structure, it is possible to display the analysis result in a shape close to the throat, which makes it easy to visually understand the analysis result.

According to aspect (11) of the invention, as shown in FIGS. 1 and 6 e.g., in the swallowing function evaluating apparatus according to any one of aspect (1) to aspect (10), preferably, the height variation detecting unit 10 includes: a projecting device 11 for projecting a plurality of bright spots in a target region; an image capturing device 12 for capturing an image of the target region having the plurality of bright spots projected therein; and an arithmetic unit 13 for calculating a variation on the basis of a shift distance δ of the image Dt of the bright spot between two frames of images 126f captured by the image capturing device 12 at different time points each other.

According to the above-mentioned structure, the height variation detecting unit includes the projecting device for projecting a plurality of bright spots, the image capturing device for capturing the image of the target region having the bright spots projected therein, and the arithmetic device. Therefore, a large scale apparatus, such as an X-ray apparatus, is not needed, and it is possible to safely and repeatedly detect a variation in height with a compact structure. In addition, this structure can reliably calculate a height variation with a small amount of computation, as compared to the structure in which simply the image of a target region is captured without projecting bright spots and an imaging process is performed on the captured image to analyze the image, thereby detecting a height variation.

According to aspect (12) of the invention, as shown in FIG. 1 e.g., preferably, the swallowing function evaluating apparatus according to aspect (11) further includes an image storage unit 23 for storing a plurality of images time-serially captured by the image capturing device 12. Preferably, the height variation detecting unit 10 calculates the variation using the stored images. In general, the capture of the image and the storage of the image are simultaneously performed in real time.

According to the above-mentioned structure, the height variation detecting unit calculates the variation using the stored image. Therefore, even when the calculation of the variation is delayed with respect to the image capturing speed, it is possible to calculate the variation on the basis of the stored image.

EFFECTS OF THE INVENTION

According to the invention, since the swallowing function evaluating apparatus comprises the height variation detecting unit for detecting a variation in a height of the surface of the throat from a predetermined reference position in the height direction in which the thyroid protrudes, it can stably and repeatedly detect the height variation without exposure to radiation. In addition, since the swallowing function evaluating apparatus includes the analyzing unit that calculate an index for evaluating the swallowing function, it can quantitatively evaluate the swallowing function on the basis of the calculated index.

This application is based on the Patent Applications No. 2006-092093 filed on Mar. 29, 2006 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

The use of the terms "a" and "an" and "the" and similar referents in the context of describing the invention (especially in the context of the following claims) are to be construed to cover both the singular and the plural, unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed.

BRIEF DESCRIPTION OF THE DRAWINGS

FIG. 2A is a left side view of a throat of an examinee, and FIG. 2B is a front view of the throat of the examinee.

FIG. 7A is a diagram schematically illustrating the image plane before the rebuilding, and FIG. 7B is a diagram schematically illustrating the image plane after the rebuilding.

FIG. 10A is a plan view schematically illustrating the image plane having the images of the rebuilt bright spots thereon, FIG. 10B is a graph illustrating the sum of height variations, which is calculated not considering the negative and positive of variations, as the distribution of the height variations, and FIG. 10C is a graph illustrating the sum of height variations, which is calculated considering the negative and positive of variations, as the distribution of the height variations.

DETAILED DESCRIPTION OF THE PREFERRED EMBODIMENT

Figure 1:
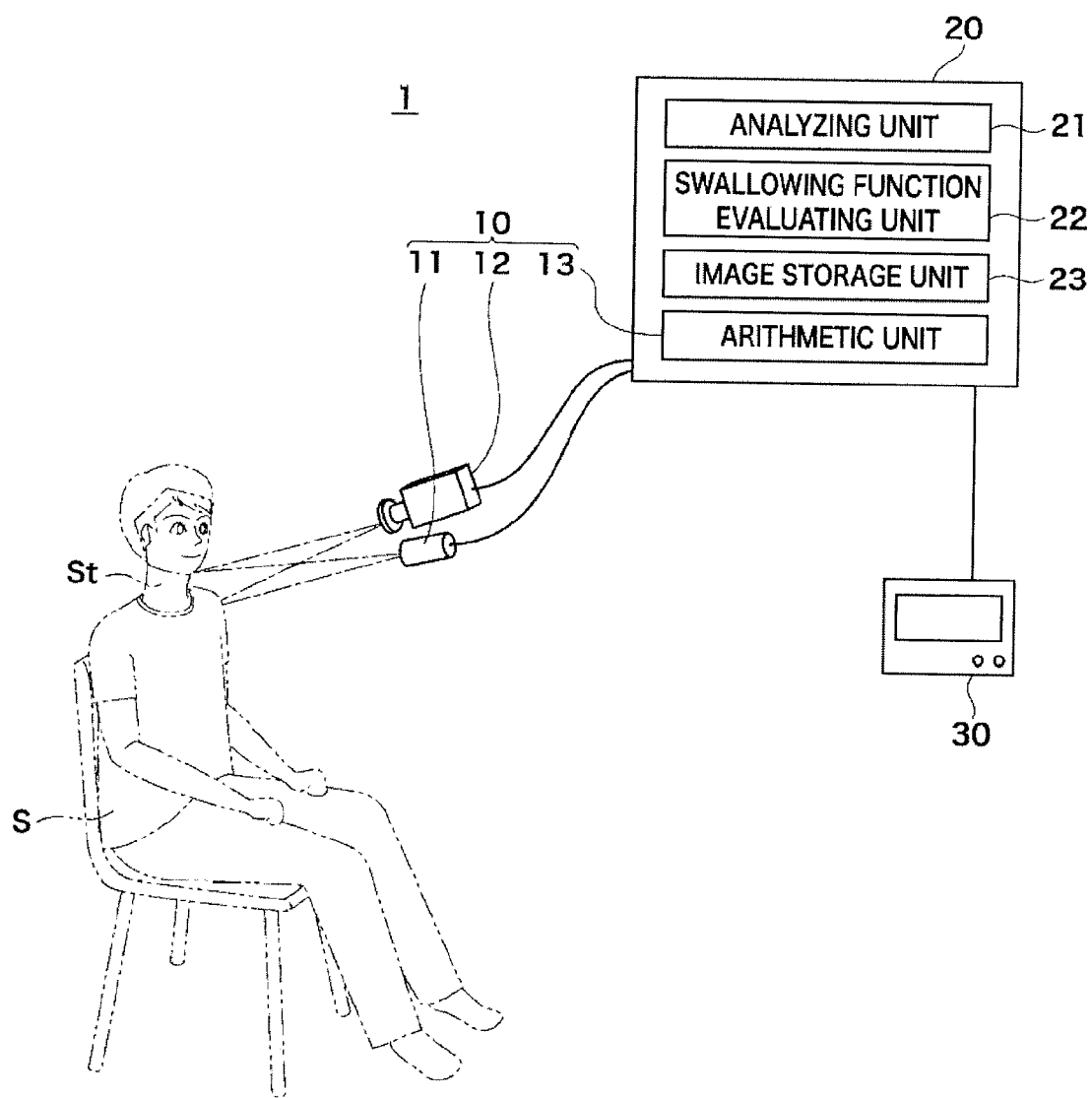
FIG. 1 is a diagram schematically illustrating the structure of a swallowing function evaluating apparatus according to an embodiment of the invention.

Hereinafter, embodiments of the present invention will be described below with reference to the accompanying drawings. In the drawings, the same or similar components have the same or similar reference numerals, and the same descriptions may not be repeated.

FIG. 1 is a drawing generally illustrating the structure of a swallowing function evaluating apparatus 1 according to an embodiment of the present invention. The swallowing function evaluating apparatus 1 comprises a fiber grating (FG) sensor 10 serving as a height variation detecting unit, an analyzing unit 21 for analyzing the detected variation in height to calculate an index for evaluating a swallowing function, a swallowing function evaluating unit 22 for evaluating the swallowing function of an examinee on the basis of the calculated index, an image storage unit 23 for storing the image captured by the FG sensor 10, and a display device 30 for visually displaying the calculated index or the evaluated result of the swallowing function. The swallowing function evaluating apparatus 1 analyzes the variation in the position of a throat St of an examinee S in the height direction that is detected by the FG sensor 10, calculates an index for evaluating the swallowing function of the examinee S to evaluate the swallowing function of the examinee S.

Figures 2A, 2B:
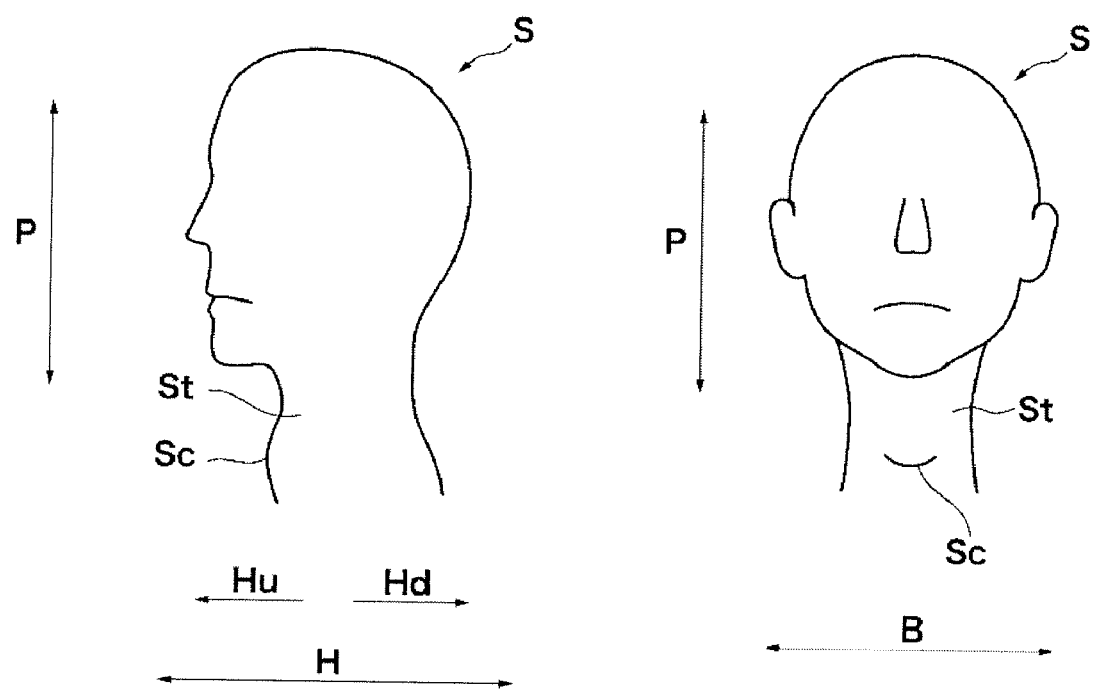
FIGS. 2A and 2B are diagrams illustrating directions. More specifically.

With reference to FIGS. 2A and 2B, directions used in this specification will be described. FIGS. 2A and 2B are drawings illustrating the directions. More specifically, FIG. 2A is a left side view of the throat St of the examinee S, and FIG. 2B is a front view of the throat St of the examinee S. In FIGS. 2A and 2B, the head of the examinee S is disposed on the upper side, and a thyroid Sc of the examinee S protrudes toward the left side of the drawing (the Adam's apple). That is, in FIG. 2A, the thyroid Sc of the examinee S protrudes in the horizontal direction, which is referred to as a height direction (which is represented by a character H). In FIG. 2A, the thyroid Sc moves in the vertical direction during a swallowing motion, which is referred to as a thyroid moving direction (which is represented by a character P). In the front view of FIG. 2B, the thyroid Sc of the examinee S protrudes in a direction of this side of the plane of the drawing (orthogonal direction to the plane of the drawing). In FIG. 2B, the horizontal direction is orthogonal to the thyroid moving direction P and the height direction H, which is referred to as a widthwise direction (which is represented by a character B). As described above, typically, the height direction H is orthogonal to the direction in which the thyroid Sc moves.

Again with reference to FIG. 1, the FG sensor 10 will be described. The term 'FG' in the FG sensor stands for fiber grating. The FG sensor 10 includes a projecting device 11 that is provided in front of the examinee S and projects a plurality of bright spots on the surface of the throat St as a target region of the examinee S, an image capturing device 12 that captures the image of the throat St having the bright spots projected thereon, and an arithmetic unit 13 that calculates a variation of the surface of the throat St in the height direction H (see FIGS. 2A and 2B) on the basis of the shift distance of the bright spot from two frames of images captured at different times among the captured images.

Figure 3:
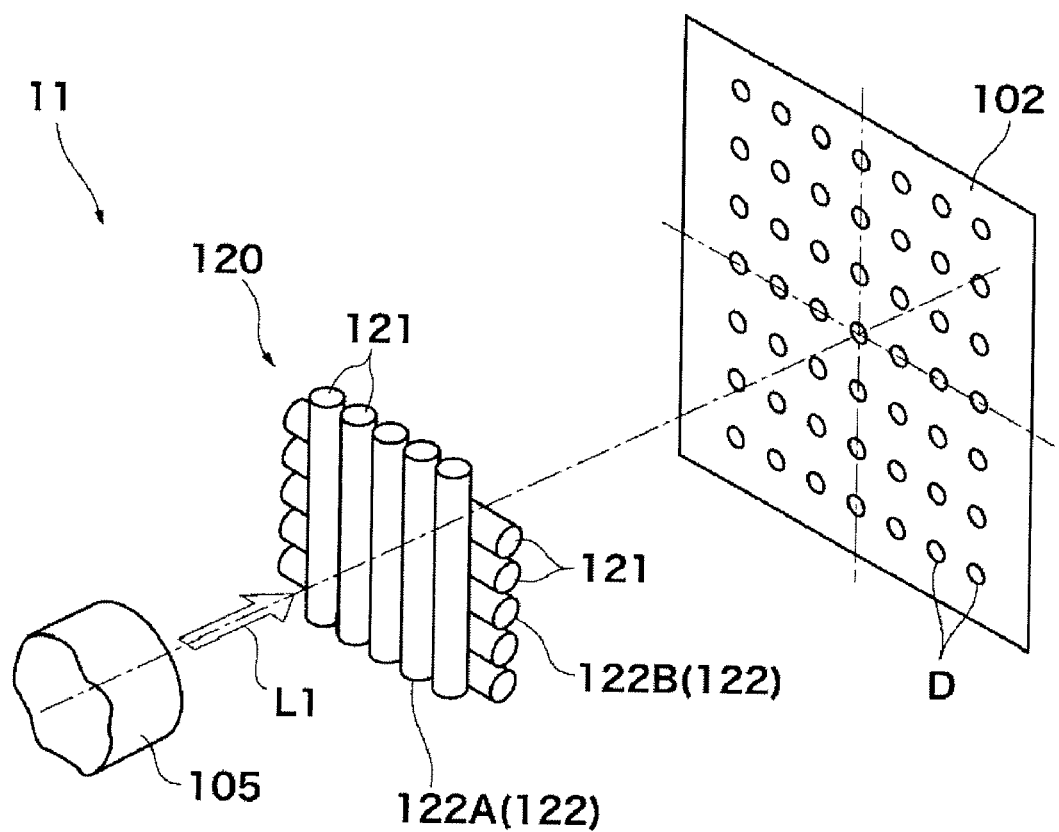
FIG. 3 is a perspective view schematically illustrating a projecting device.

With reference to FIG. 3, the general structure of the projecting device 11 will be described below. FIG. 3 is a perspective view schematically illustrating the projecting device 11. The projecting device 11 includes a light beam generating unit 105 for generating coherent light beams and a fiber grating 120. The light beam generating unit 105 is typically a semiconductor laser device including a collimator lens (not shown), and generates parallel laser beams L1. The parallel beams include perfectly parallel beams and substantially parallel beams. The laser beams L1 have substantially circular shapes in sectional view. The substantially circular shapes include elliptical shapes. The coherent light beams emitted by the light beam generating unit 105 are typically near infrared laser beams.

The fiber grating 120 includes two FG elements 122 (122A and 122B) each composed of about 100 optical fibers 121 that are arranged in parallel into a sheet shape, and the two FG elements 122A and 122B are arranged such that the surfaces thereof are parallel to each other and the optical fibers 121 of the FG element 122A are orthogonal to the optical fibers 121 of the FG element 122B. The number of optical fibers 121 of the FG elements 122A and 122B may increase or decrease according to usage conditions. The FG element 122A and the FG element 122B may be disposed so as to contact each other, or they may be disposed separately from each other in the normal direction of the surfaces thereof. Each of the optical fibers 121 typically has a diameter of about 2 μm to 50 μm and a length of about 10 mm, but the diameter and length of the optical fiber 121 are not limited thereto. The diameter and length of the optical fiber 121 may vary adapting to the usage conditions.

The projecting device 11 having the above-mentioned structure projects a plurality of bright spots by the following method. The laser beam L1 generated by the light beam generating unit 105 is incident on the fiber grating 120 so as to be orthogonal to the surfaces of the FG element 122A and the FG element 122B. Then, each of the optical fibers 121, serving as a cylindrical lens, condenses the laser beam L1 on the focal point thereof, and a plurality of divergent waves are generated. Then, the divergent waves travel while interfering with each other. As a result, as shown in FIG. 3, bright spots D are projected on a projecting surface 102 parallel to the surface of the FG element 122 at regular intervals. The throat St (see FIG. 2) of the examinee S, as a target region of the swallowing function evaluating apparatus 1, is not flat, but the projecting surface 102, which is a target region, is shown as a flat surface in FIG. 3 for the purpose of easy understanding of the principle of the FG sensor 10.

As described above, since the projecting device 11 is an optical system including the fiber grating 120 having the two FG elements 122A and 122B and the light beam generating unit 105, the structure of the optical system is simplified, which makes it possible to reduce the size of the optical system. In addition, since the projecting device 11 uses the fiber grating 120, the structure of the projecting device 11 can be simplified and can project a plurality of bright spots D onto a plane target region in a square lattice shape at regular intervals. In this case, the shape of the bright spot is a substantially circular shape (including an elliptical shape).

Figure 4:
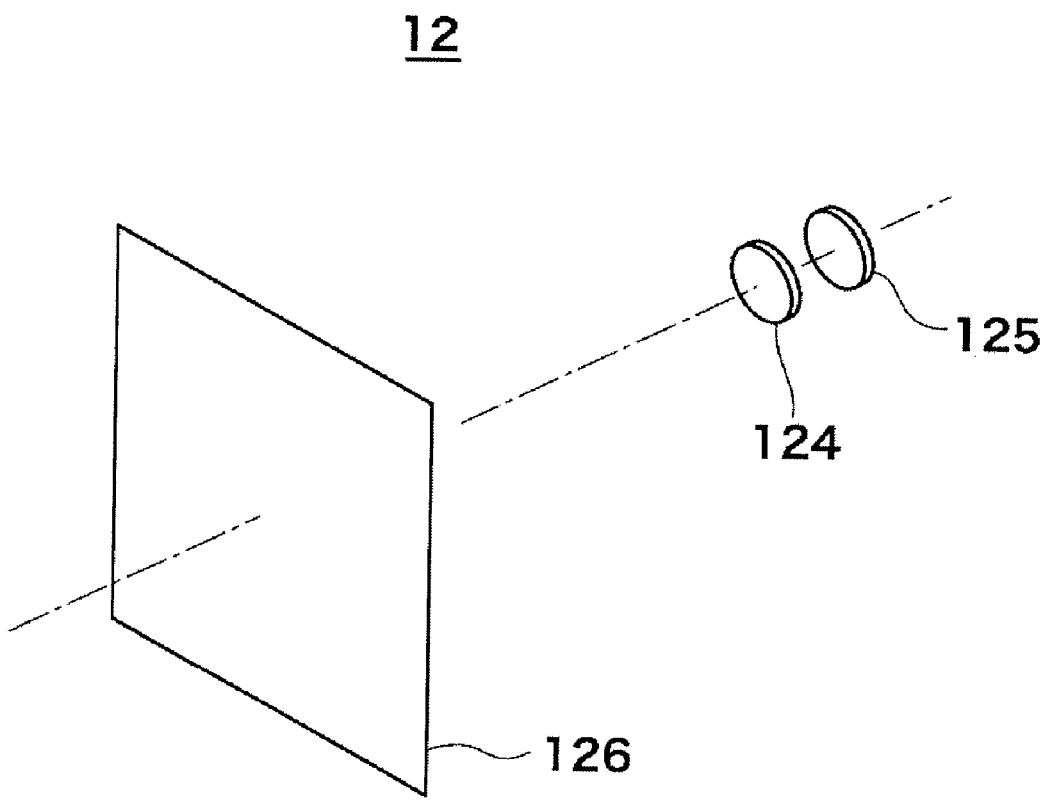
FIG. 4 is a perspective view schematically illustrating an image capturing device.

Next, with reference to FIG. 4, the general structure of the image capturing device 12 will be described. FIG. 4 is a perspective view schematically illustrating the image capturing device 12. The image capturing device 12 includes an image forming lens 124, serving as an image forming optical system, and an image capturing element 126. The image sensor 126 is typically a CCD image sensor. In general, the CCD image sensor is of a high-sensitivity and with smaller noise, as compared to the other image sensors (image capturing elements). A CMOS element having lower power consumption and lower manufacturing costs than the CCD image sensor may be used as the image capturing element 126. The image capturing device 12 preferably includes a filter 125 that reduces light components having different wavelengths from those of the laser beams L1 emitted from the light beam generating unit 105 (see FIG. 3). The filter 125 is an optical filter, such as typically an interference filter, and is preferably arranged on the optical axis of the image forming lens 124. In this way, the image capturing device 12 can reduce the influence of disturbance light since the intensity of light at the bright spot D projected by the projecting device 11 becomes relatively high among the light components received by the image capturing element 126.

Again with reference to FIG. 1, the FG sensor 10 will be described. The arithmetic unit 13 calculates the shift of the image of the bright spot between two frames of images captured at two different times by the image capturing device 12. The images captured at two different times are a captured image (an N-th frame) and a reference image (an (N−1)-th frame) captured immediately before the captured image, or the captured image (the N-th frame) and a fixed reference image (an Ns frame) at a fixed reference time. The reference image (the (N−1)-th frame) may be an image that is captured a predetermined time before the captured image. The time interval to capture a continuous series of images may be determined in consideration of the processing time of the apparatus, and the moving speed of the thyroid of the throat, which is a target region. The time interval of image capture may be as short as possible and averaging and filtering may be performed on the captured image, thereby reducing the influence of random noise e.g. In this embodiment, the time interval of image capture is set to an equal interval of 1/30 second in consideration of the above-mentioned factors. A variation in height that is acquired at equal intervals may be considered as speed. When the variation in height is divided by 1/30 second, (movement per second) is obtained. The arithmetic device 13 calculates the variation in height in a target region (the projecting surface 102 (see FIG. 3)) on the basis of the concept of the detection of the variation in height using the FG sensor 10. The arithmetic device 13 is typically a CPU of a computer 20.

Figure 5:
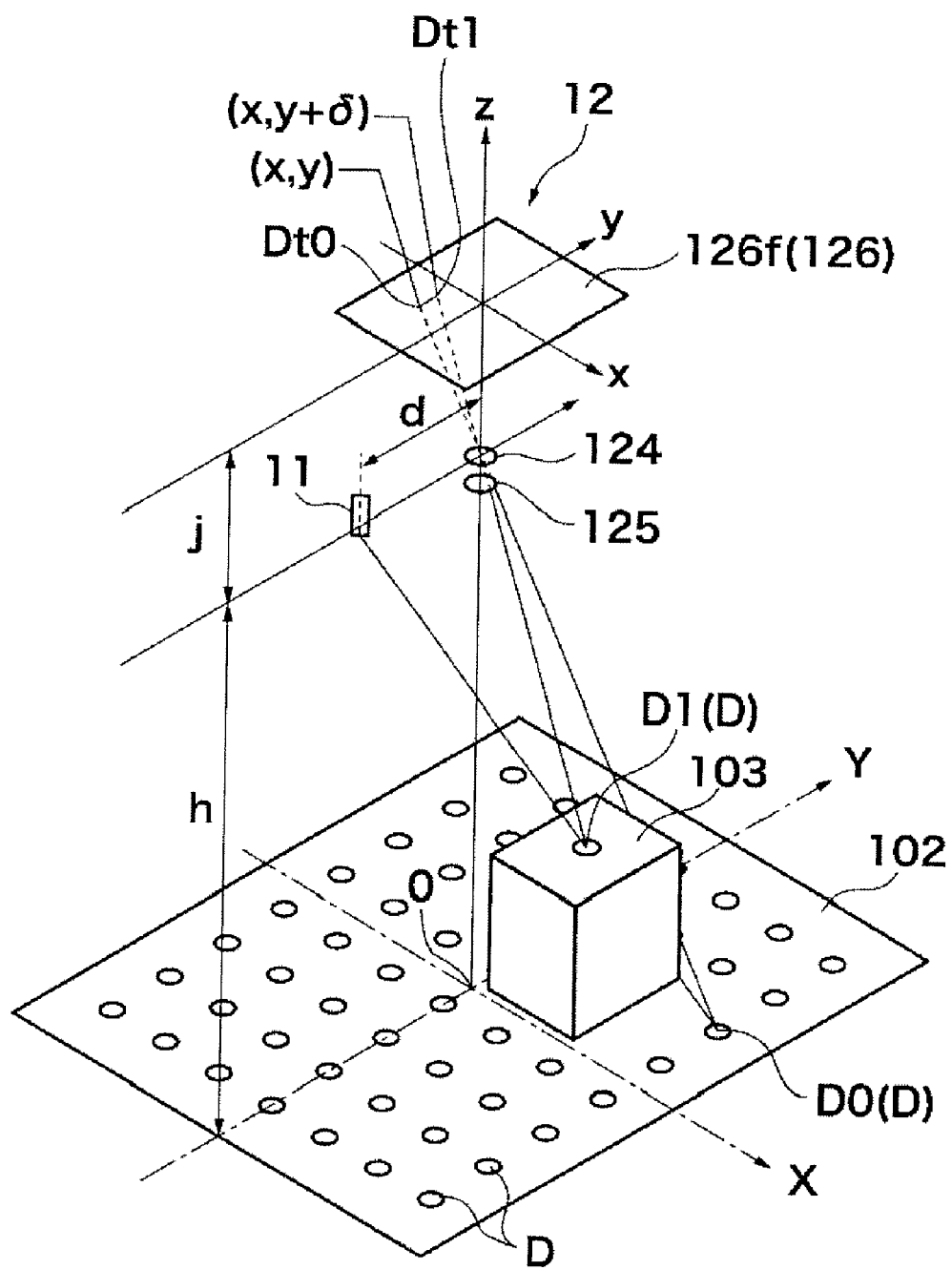
FIG. 5 is a perspective view schematically illustrating the concept of the detection of a variation.

With reference to FIG. 5, the positional relationship between the projecting device 11 and the image capturing device 12 and the concept of the detection of the variation using the FG sensor 10 will be described. FIG. 5 is a perspective view schematically illustrating the concept of the detection of the variation. In FIG. 5, for the purpose of convenience of explanation, the target region having the bright spots D projected thereon and to be photographed is considered as the flat projecting surface 102. An orthogonal coordinate system XYZ is used for the projecting surface 102 so that an X-axis and a Y-axis are arranged on the projecting surface 102. The image capturing device 12 is arranged above the projecting surface 102 such that the optical axis of the image forming lens 124 is aligned with the Z-axis. An image plane 126f of the image capturing element 126 is arranged on the Z-axis so as to be orthogonal to the Z-axis. An xy orthogonal coordinate system is established on the image plane 126f with the Z-axis passing through the origin. The distance between the projecting surface 102 and the image forming lens 124 in the Z-axis direction is set to h. The distance between the imaging lens 124 and the image plane 126f in the Z-axis direction is set to j. The projecting device 11 is arranged so as to be separated from the image capturing device 12 by a distance d in the negative Y-axis direction (the distance between the projecting surface 102 and the projecting device 11 in the Z-axis direction is set to h). The distance d is the length of a base line. That is, the FG sensor 10 uses triangulation to detect a variation in the height direction (the Z-axis direction in FIG. 5) on the projecting surface 102 on the basis of the shift distance of the image of the bright spot on the image plane 126f. The concept of the detection of the variation in the height direction will be described below.

In the concept of the detection of the variation in the height direction, it is assumed that the reference image (the (N−1)-th frame) or the fixed reference image (the Ns-th frame) is the image of the bright spots D when no object exists on the projecting surface 102, and the captured image (the N-th frame) is the image of the bright spots D when an object 103 exists on the projecting surface 102. In addition, it is assumed that the object 103 is arranged in the first quadrant in the XY coordinates. The image of the bright spots D that appears at regular intervals in the x-axis direction and the y-axis direction of the image plane 126f exists on the reference image. On the other hand, in the captured image, among the bright spots D to be projected onto the projecting surface 102, a bright spot D1 to be projected onto a portion of the projecting surface 102 where the object 103 exists is shielded by the object 103, so that it does not reach the projecting surface 102. In this case, the bright spot D to be projected onto a point D0 on the projecting surface 102 but for the object 103, is projected onto the point D1 on the object 103. Then, the bright spot D shifts from the point D0 to the point D1, and the imaging lens 124 is separated from the projecting device 11 by the distance d (the length d of the base line). As a result, the bright spot to be image-formed at a point Dt0 (x, y) is image-formed at a point Dt1 (x, y+δ) on the image plane 126f. That is, the image Dt of the bright spot D shifts by the distance δ in the y-axis direction due to the existence of the object 103.

Figure 6:
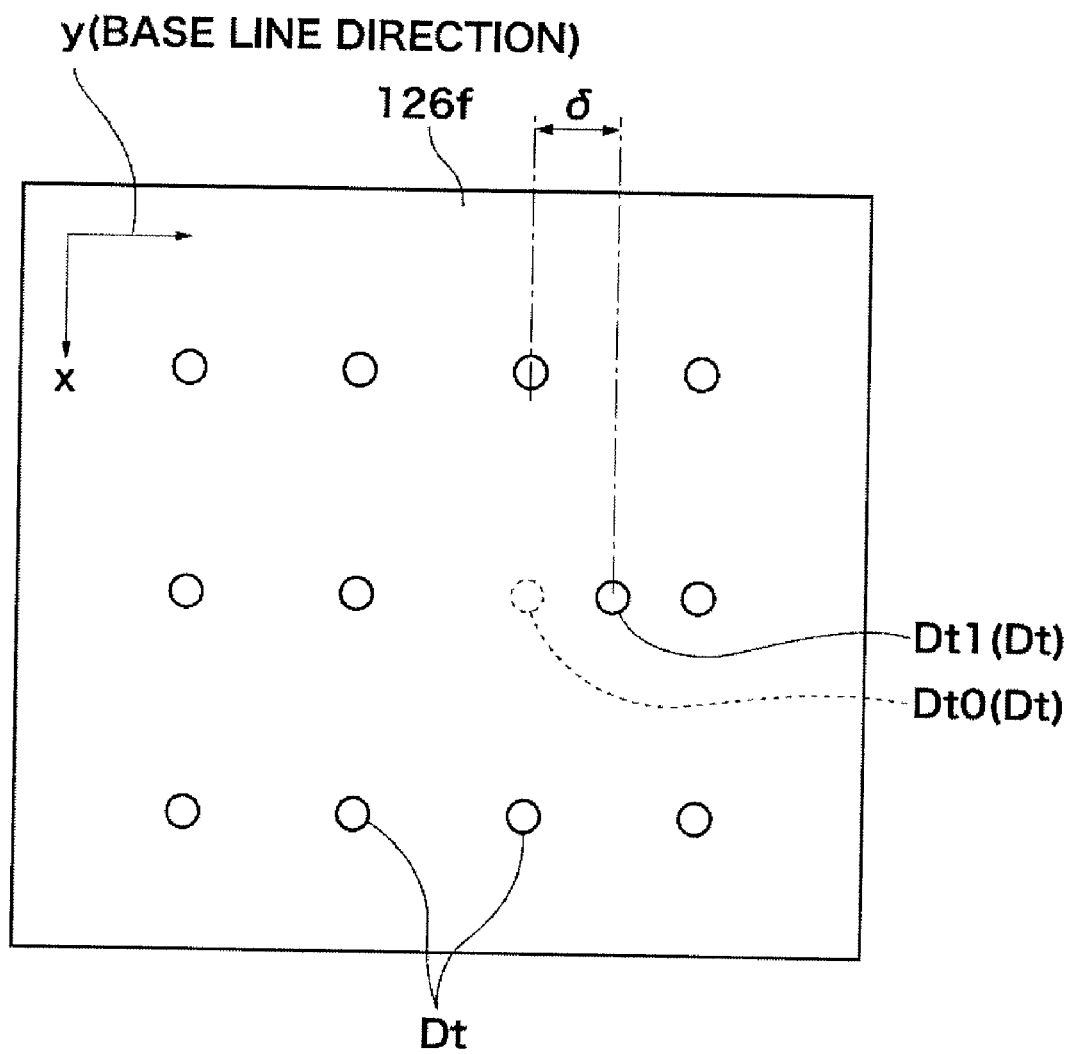
FIG. 6 is a plan view of an image plane of the image capturing device.

FIG. 6 is a plan view of the image plane 126f. As shown in FIG. 6, among the images of the bright spots Dt formed on the image plane 126f, the image Dt1 affected by the object 103 moves by the distance δ in the y-axis direction due to the protruding object 103. The shift δ of the image Dt of the bright spot on the imaging surface image plane 126f is calculated in this way, which makes it possible to three-dimensionally specify the position of the point D1 on the object 103. The relationship between the movement distance Z of the object 103 in the height direction on the projecting surface 102 and the distance δ of the image Dt of the bright spot on the image plane 126f is represented by Expression 1 given below:

$$\delta = djZ / \{h(h-Z)\} \quad (1)$$

In this way, the height Z of the point D1 is found. As described above, it is possible to detect a variation in the height of the object 103 by calculating the distance between the point Dt0 to be image-formed onto the image plane 126f but for the object 103 and the actual image forming position Dt1 on the image plane 126f. In this case, when the pitch between the bright spots D is narrowed to such an extent that the correspondence between the bright spot D in the reference image and the bright spot D in the captured image is not unclear, it is possible to minutely detect a variation in the height of the object 103. The variation between the captured image and the fixed reference image may be calculated by accumulating variations between the captured image and the reference image in time series. However, the variation between the captured image and the fixed reference image is preferably calculated by accumulating variations between the captured image and the reference image in time series in such cases that errors are not accumulated as calculating the variation between the captured image and the reference image.

The detection accuracy of the shift distance δ of the image Dt of the bright spot depends on the length d of the base line (which is equal to the distance d between the image forming lens 124 and the projecting device 11). From the principle of triangulation, as the length d of the base line becomes larger, the shift δ of the image Dt of the bright spot on the image plane 126f relative to the variation in the height of the object in the target region 102 becomes larger, which makes it possible to detect a minute variation in the height of the object in the target region 102. However, when the length d of the base line is large and the variation in the height of the object in the target region 102 is excessively larger than the interval between the bright spots radiated, the bright spot D1 jumps over an adjacent bright spot D, which causes the FG sensor to determine that the bright spot D1 shifts from the adjacent bright spot D and thus to erroneously detect a variation in height. On the other hand, when the length d of the base line is small, the bright spot hardly jumps over an adjacent bright spot, but the shift δ of the image Dt of the bright spot on the image plane 126f becomes small, which makes it difficult to discriminate a minute variation in height in the target region 102 from noise. Preferably, the length d of the base line is determined considering the above-mentioned advantages and disadvantages. However, in this embodiment, the swallowing motion for detecting a variation in height is completed with several seconds, and the FG sensor 10 for detecting the variation in height in the swallowing motion captures 30 images per second. Consequently, the shift δ of the image Dt of the bright spot between two adjacent frames is relatively small. Therefore, in the FG sensor 10 according to this embodiment, it is possible to increase the length d of the base line without jumping over the bright spot D.

When obtaining a variation in height between when the fixed reference image is acquired and when the captured image is acquired, the variations in height may be accumulated on the basis of a plurality of the reference images and the captured images acquired in the period from when the fixed reference image is acquired to when the captured image is acquired, but the variation in height may be directly calculated from the fixed reference image and the captured image. In this case, the image of the bright spot is not searched in the captured image within the range in which the image of the bright spot can move between the interval between the images of the bright spots in the fixed reference image, but each of the images of corresponding bright spots is searched between two continuous frames to be acquired plural times between the time when the fixed reference image is acquired and the time when the captured image is acquired. Then, this process is repeatedly performed to trace the image of the bright spot, which makes it possible to establish the accurate correspondence between the images of the bright spots even when a large amount of shift of the image of the bright spot occurs between the fixed reference image and the captured image. As a result, it is possible to reduce the possibility that a variation in height will be erroneously detected due to the jumping-over of the image of the bright spot.

With reference to FIGS. 5 and 6, in this paragraph, the description of this embodiment will be made. Plane coordinates (X, Y) of the bright spot D can be calculated by Expressions 2 and 3 given below, using plane coordinates (x, y) of the image Dt of the bright spot and the height Z of the bright spot D calculated by Expression 1, and the three-dimensional position of the bright spot D can be detected:

$$X=x(h-Z)/j \quad (2)$$

$$Y=(y+\delta)\cdot(h-Z)/j \quad (3)$$

However, when the shift δ of the image Dt of the bright spot is smaller than the distance h between the projecting surface 102 and the image forming lens 124 in the Z-axis direction or the product dj of the distance d between the projecting device 11 and the imaging capturing device 12 in the Y-axis direction and the distance j between the imaging lens 124 and the image plane 126f in the Z-axis direction, the shift δ of the image Dt of the bright spot is assumed to be proportional to the height Z of the bright spot D, and a value obtained by multiplying the shift δ by a constant (including 1) may be used as a variation in height, and coordinates obtained by multiplying the plane coordinates (x, y) of the image Dt of the bright spot by a constant (including 1) may be used as the plane coordinates (X, Y) of the bright spot D.

Again with reference to FIG. 1, the swallowing function evaluating apparatus 1 will be described, where referring to FIG. 2 about the directions, and referring to FIGS. 5 and 6 about the image plane. In order to evaluate the swallowing function of the examinee S, as described above, the FG sensor 10 emits the bright spots D to the throat St of the examinee S by, and captures the image including of the throat St on which the bright spots D are radiated. When the projecting device 11 projects the bright spots, a plurality of bright spots Dare projected in the widthwise direction B and the direction P in which the thyroid moves, and thus the images Dt of the plurality of bright spots also appear on the captured image 126f. In this case, since each of the images Dt of the bright spots in the captured image has a size, it is preferable to specify the representative position of the bright spot D in the coordinates (a reference position) such that numerical processing can be performed when a variation in height is calculated. Therefore, it is preferable to calculate the center of gravity of the image Dt of each of the bright spots as a representative point which can be stably and easily calculated and is suitable for the numerical processing, and calculate the shift distance of the image Dt of the bright spot using the center of gravity as a reference point. In this way, it is possible to calculate the position of the image Dt of the bright spot with sub-pixels smaller than pixels of the captured image and thus accurately detect a variation in height.

In order to calculate the center of gravity of the image Dt of the bright spot, first, an cumulative histogram for the overall brightness of the captured image is prepared, and a brightness corresponding to a predetermined percentage (for example, 95%) is set as a threshold value. Then, the outline of the image Dt of the bright spot is determined in such a manner that a portion of the image whose brightness is lower than the threshold value has no bright spot and another portion of the image whose brightness is equal to or higher than the threshold value has a bright spot (floating threshold processing). In this case, for example, preferably, the portion having no bright spot is digitized to 0, and the portion having the bright spot is digitized to 255, adapted to the computer processing. When the outline of the image Dt of the bright spot is determined, the center of gravity (centroid) of the image Dt of the bright spot is calculated on the basis of the outline. Typically, the center of gravity of the image Dt of the bright spot is calculated by dividing a geometrical moment of area related to reference axes (in this embodiment, an x-axis and a y-axis) on the image Dt of the bright spot by the area of the image Dt of the bright spot. The arithmetic device 13 calculates the center of gravity of the image Dt of the bright spot.

The FG sensor 10 is disposed such that the image capturing device 12 captures the image of the bright spots D projected onto the throat St of the examinee S by the projecting device 11 (that is, the throat St is a reference). The bright spots D emitted to the throat St appear as the images Dt of the bright spots in the reference image or the fixed reference image, and a variation in the height of the throat St can be detected by the shift distance δ of the image Dt of the bright spot (see Expression 1). In this case, a predetermined search range in which the image Dt of the bright spot shifts is provided, and the image Dt of the bright spot on the captured image corresponding to the image Dt of the bright spot on the fixed reference image is searched in the predetermined search range. Ideally, the predetermined search range is narrow in the direction vertical to the base line and is wide in the direction parallel to the base line, considering that the image Dt of the bright spot moves only in the direction parallel to the base line due to a variation in the height of the bright spot D. Typically, the range from an image Dt of bright spot to the central position between the image Dt and another image of adjacent bright spot in the reference image or the fixed reference image is the maximum search range. Here, the image Dt of the bright spot in the captured image that is detected in the search range is called a shifting spot. On the other hand, when the image Dt of the bright spot is not detected within the search range, the image Dt of the bright spot is called an extinct spot. The extinct spot occurs when the bright spot D radiated onto the wall at the rear of the examinee S or the head of the examinee S, which has the low reflection intensity of the bright spot, is not detected as the image Dt of the bright spot on the image plane 126f, or it occurs due to a lack of uniformity in the reflectance or angle of a portion of the throat St of the examinee S onto which the bright spot D is radiated.

The arithmetic device 13 calculates to detect a variation in the position of the image of each bright spot on the surface of the throat St in the height direction from a predetermined reference position, from the shift distance δ of the image Dt of the shifting spot between two frames, on the basis of the relationship between the variation in the height direction H based on the above-mentioned concept and the shift in the position of the image of each bright spot. The surface of the throat St is typically the skin of the throat St. The predetermined reference position is typically a fixed position on the surface of the throat in the height direction, but it may be the position of the surface of the throat St in the height direction that is detected from a just previously captured image among the images continuously captured. The fixed reference position is typically the position of the surface of the throat St in the height direction during breathing (when the swallowing motion is not performed).

As described above, a variation in the height of the surface of the throat St is calculated at a plurality of points. However, since the surface of the throat St to which the bright spots D are emitted is an uneven surface, not a flat surface, the images Dt of the bright spots in the captured image are not arranged in an orderly matrix, as shown in FIG. 6.

Figure 7A:
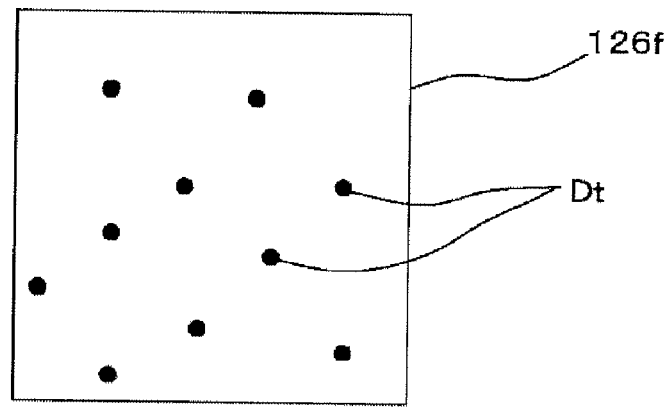
FIGS. 7A and 7B are diagrams illustrating the rebuilding of the images of bright spots.
Figure 7B:
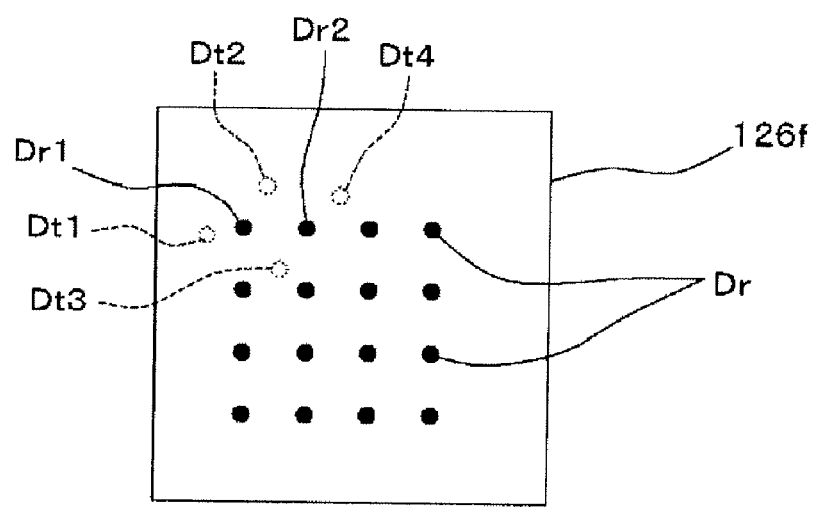

As shown in FIG. 7A, when the bright spots D are radiated onto the uneven surface of the throat St and the images of the bright spots D are captured, the images Dt of the bright spots are irregularly arranged on the captured image 126*f*. It is preferable that a variation in height calculated from the images Dt of the bright spots that are irregularly arranged is rebuilt to a variation in the height of bright spots Dr arranged in an orderly matrix as shown in FIG. 7B, in order to easily perform the subsequent analyzing and evaluating process. In the rebuilding, typically, the bright spots Dr arranged at predetermined intervals (for example, at a five-pixel interval) are first determined, and next a variation in the height of the bright spots Dr is calculated from the images Dt of a plurality of bright spots close to the spot Dr to be rebuilt (for example, the images Dt of three different bright spots close to the bright spot Dr to be rebuilt) by linear interpolation. The rebuilding will be described in detail below e.g. with reference to FIG. 7B. For example, when a spot Dr1 is rebuilt, a variation in the height of the spot Dr1 is calculated from variations in the height of the images Dt1, Dt2, and Dt3 of three bright spots close to the spot Dr1 by linear interpolation. When a spot Dr2 is rebuilt, a variation in the height of the spot Dr2 is calculated from variations in the height of the images Dt2, Dt3, and Dt4 of three bright spots close to the spot Dr2 by linear interpolation. The invention is not limited to the linear interpolation using three bright spots. For example, a least squares method using a plurality of bright spots close to a spot to be rebuilt may be used.

Further, variations in the position of the surface of the throat St in the height direction at a plurality of points may be visualized and sensuously apprehend to facilitate the understanding of the analysis result, which will be described later. For example, the following method may be used: a variation in the height of the rebuilt spot Dr is represented in a convex or concave shape with respect to the tentative reference plane (when the variation is positive, the variation is represented in a convex shape, and when the variation is negative, the variation is represented in a concave shape), and the display device 30 (see FIG. 1) displays the concave and convex shape. For example, a concave portion and a convex portion may be displayed in different colors in a wire frame (a method of representing the outline of a three-dimensional figure with only lines), which makes it possible to clearly discriminate the concave portion from the convex portion. In this case, when a cylindrical surface, not a flat surface, is used as a reference surface and concave and convex portions are formed in the cylindrical surface, it is easy to simulate the throat and sensuously image the throat. Therefore, this method is preferable.

Figure 8:
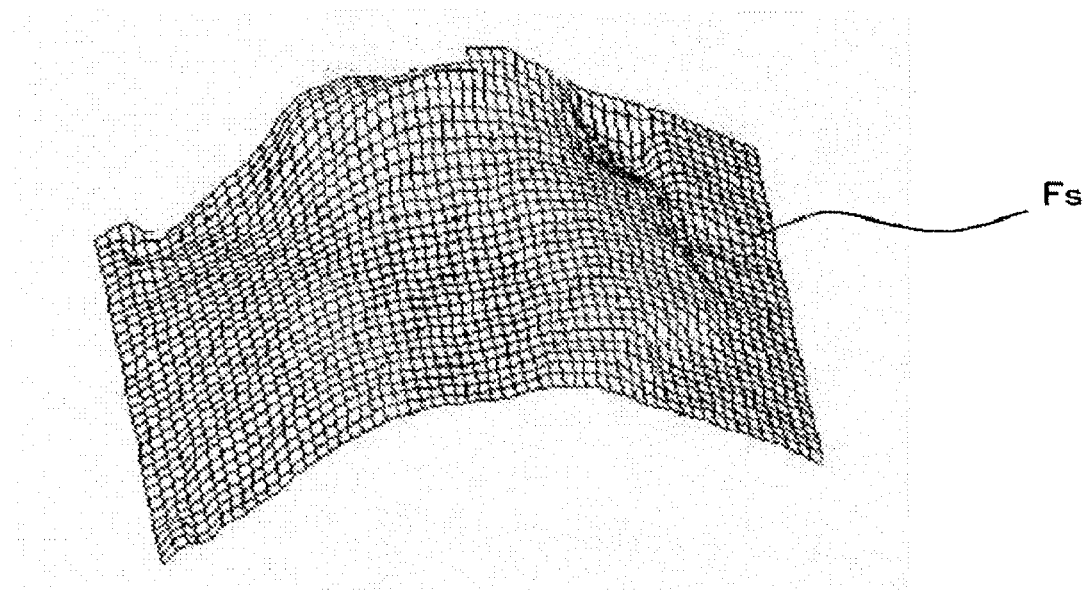
FIG. 8 is a diagram schematically illustrating a height variation displayed on a reference surface of a cylindrical surface.

FIG. 8 shows an example of a variation in the height of the surface of the throat St that is displayed on a cylindrical reference surface Fs. Concave and convex portions, as can be seen in FIG. 8, indicate positions with a variation in height.

Analysis Example 1

In a first analysis example for calculating an index for evaluating a swallowing function from a variation in the height of the surface of the throat St detected in the above-mentioned method, the height of the surface of the throat St during breathing is fixed as a reference height, and the length between two points, which are both ends of a portion having a large variation in the height of the surface of the throat St in the direction P in which the thyroid moves in a series of swallowing motion, is calculated. From the characteristics of the throat St, the movable range of the thyroid Sc is the range in which the variation in height is large.

Figure 9:
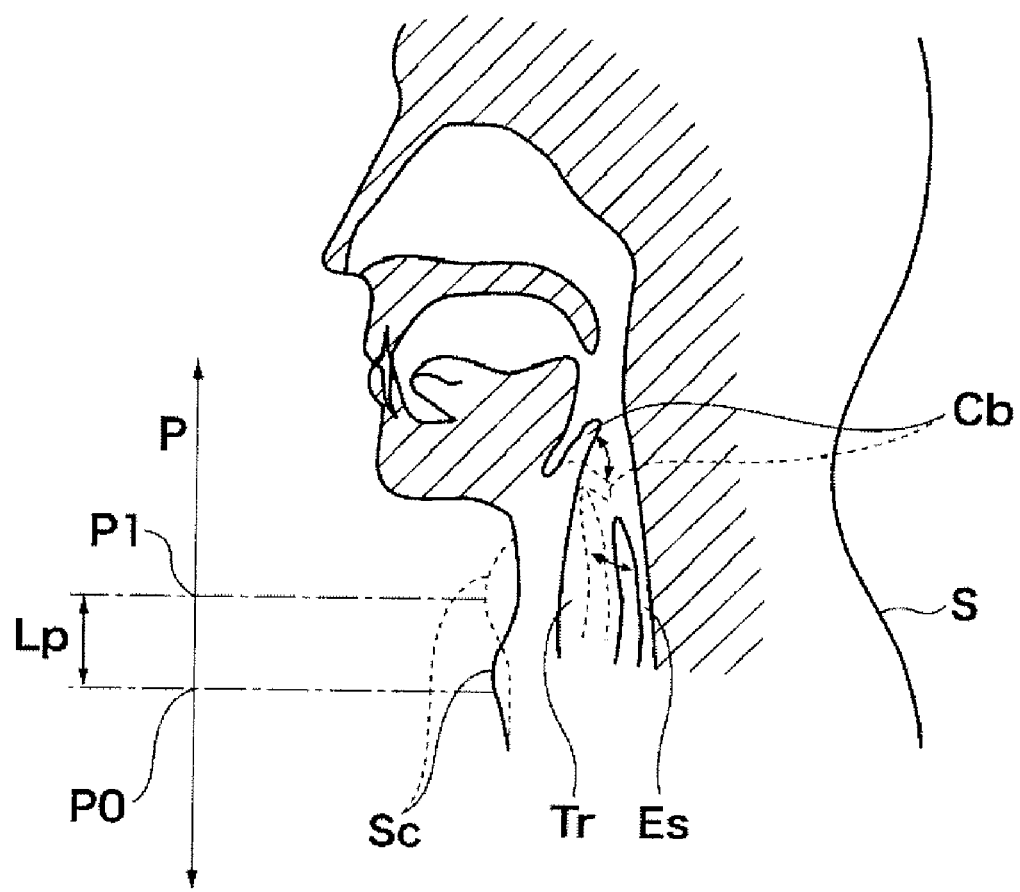
FIG. 9 is a diagram illustrating the movement distance of a thyroid.

As shown in FIG. 9, the thyroid Sc is disposed at a position P0 at the chest side (the lower side of the drawing) during breathing. The thyroid Sc moves to a position P1 at the head side (the upper side of the drawing) and then returns to the position P0 at the chest side as a swallowing motion. The distance Lp between the position P0 and the position P1 is the distance between two points, that is, both ends of a portion having a large variation in height in the direction P in which the thyroid moves. When the thyroid Sc is at the position P0, which is a reference position, the variation in height is zero. When the thyroid Sc is at the position P1, the variations in height from the reference position is the largest at both positions P0 and P1. However, as the positive and negative values of the coordinate axis shown in FIG. 6 are considered, the variation in height at the position P1 from the reference position has a positive maximum value, and the variation in height at the position P0 from the reference position has a negative maximum value.

The distance Lp can be used as an index for evaluating the swallowing function. When a person without a swallowing disorder swallows food, the thyroid Sc is lifted up by the muscular strength of the throat to drop an epiglottis Cb, and then the trachea Tr is temporarily closed, which prevents food and drink from getting into the trachea Tr. However, as can be seen from a patient suffering from a muscular dystrophy or myasthenia, when the muscular strength of the throat is weakened, the thyroid Sc is not completely lifted up and thus the trachea Tr is not sufficiently closed by the epiglottis Cb, which causes food and drink to get into the trachea Tr, not the gullet Es. As such, it is estimated that the distance Lp corresponding to the movement distance of the thyroid Sc is correlated with existence of the swallowing disorder. When a doctor diagnoses the swallowing disorder on the basis of the index, it is possible to quantitatively evaluate the swallowing function. Alternatively, a difference in the distance Lp between a person suffering from the swallowing disorder and a person not suffering from the swallowing disorder may be examined beforehand and stored in the swallowing function evaluating unit 22 (see FIG. 1), and the swallowing function of an examinee may be evaluated on the basis of the analysis result referred to the swallowing function evaluating unit 22. The swallowing function evaluating unit 22 is typically composed of a memory and a CPU of a computer. In many cases, the relationship between the distance Lp and the existence or nonexistence of the swallowing disorder depends on factors, such as the age, sex, and body type of an examinee. Therefore, preferably, the storage should be done individually for each factor in the swallowing function evaluating unit 22 beforehand, and those factor data for the examinee are input to the swallowing function evaluating apparatus 1 (see FIG. 1) to evaluate the swallowing function of the examinee at the time of examination. The method can quantitatively evaluate the swallowing function both when the doctor diagnoses the swallowing disorder on the basis of the obtained index and when the swallowing function is evaluated on the basis of data stored beforehand.

Analysis Example 2

In a second analysis example, in each captured frame of images continuously captured (at a point of time during the swallowing motion), variations in the height of the bright spots at separate rows each other arranged with a predetermined interval in the direction P in which the thyroid moves, the variations being from a fixed reference image (typically, a reference image during breathing), are added up (projection: one-dimensional projection) all the way across along the widthwise direction B. The addition may preferably be performed using the rebuilt spots Dr (see FIG. 7B). In this case, the predetermined intervals in the direction P in which the thyroid moves may be intervals of the spots Dr. The predetermined interval may not be constant. For example, however, when the interval in the portions having a large variation in height is narrowed, the accuracy of analysis increases. When the interval is constant, the analysis can be easily performed.

Figure 10A:
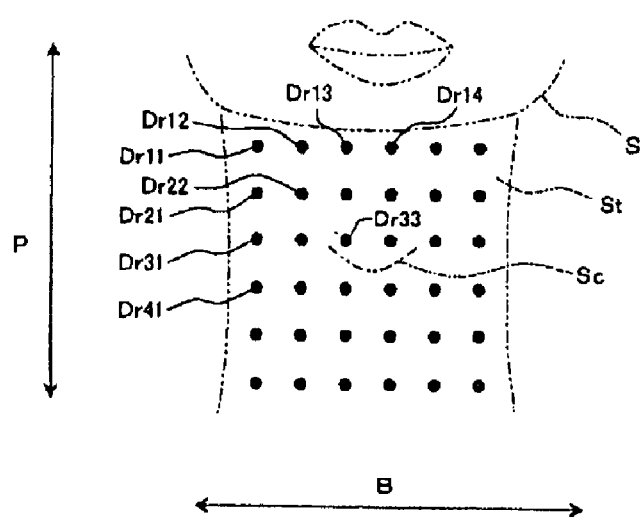
FIGS. 10A to 10C are diagrams illustrating the addition of height variations.

With reference to FIG. 10A, the addition of height variations at a certain point of time will be described. When a variation in the height of the spot Dr11 is $\delta 11$, a variation in the height of the spot Dr12 is $\delta 12$, and a variation in the height of the spot Drij is $\delta ij$, the sum S1 of variations in the height of a first row of spots is as follows:

$$S1 = \Sigma \delta 1j = \delta 11 + \delta 12 + \ldots + \delta 1j$$

Similarly, the sum S2 of variations in the height of a second row of spots separated from the first row of spots by a predetermined interval in the direction P in which the thyroid moves is as follows:

$$S2 = \Sigma \delta 2j = \delta 21 + \delta 22 + \ldots + \delta 2j$$

Figure 10B:
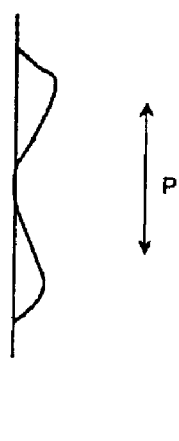

Similarly, the each sum of variations in the height of a each row of moving spots is calculated. FIG. 10B is a graph illustrating the sums of height variations at a certain point of time as the distribution of height variations.

The graph illustrating the distribution of the sum of height variations shown in FIG. 10B may be made for each of the acquired frames, and it may be determined whether the sum of height variations satisfies a predetermined condition, thereby evaluating the swallowing function. For example, the following determination may be performed to evaluate the swallowing function: it is determined whether the maximum value of the sums of height variations is equal to or larger than a threshold value; whether the maximum value of the variation of the sum in a predetermined period is equal to or larger than a threshold value; or whether the ratio of the maximum value of the variation of the sum in a predetermined period to the maximum value of the sum of height variations is equal to or larger than a predetermined value. In addition, from a feature of the variation of the sum, a neural network or recognition algorithms other than the neural network may be used to determine whether the sum of height variations satisfies a predetermined condition. It is estimated that the distribution of the sum of height variations is correlated with the movement of the thyroid Sc. Therefore, a value capable of discriminating a person suffering from the swallowing disorder from a person not suffering from the swallowing disorder or a value indicating the degree of the swallowing disorder is beforehand examined as the threshold value or the predetermined value and is then stored in the swallowing function evaluating unit 22 (see FIG. 1), and the swallowing function of the examinee is evaluated on the basis of the analysis result referred to the swallowing function evaluating unit 22. The doctor, not the computer, may diagnose the swallowing disorder on the basis of the index. In this case, the swallowing function evaluating unit 22 is not needed. The distribution of the sum of height variations is graphed to visualize the sum of height variations. Therefore, when the computer uses numerical contrast to evaluate the swallowing function, the sum of height variations does not need to be graphed.

Analysis Example 3

In FIG. 10A, in general, particularly in the head side, a portion of the throat St rises at the vicinity of the center of the row in the widthwise direction B, but at the both ends thereof it drops during the swallowing motion. In this case, when variations in the height of spots from the fixed reference image are added up, an increasing height variation in the vicinity of the center of the row in the widthwise direction B cancels a decreasing height variation at the both end sides of the row, which may cause the height variation not to appear on the graph. In this case, according to the third analysis example, preferably, variations in the height of spots from the fixed reference image are separately added up in the direction Hu (see FIG. 2) in which the thyroid Sc protrudes and the opposite direction Hd (see FIG. 2) of the direction Hu. That is, in this preferable embodiment, variations in the height of spots in the direction Hu in which the thyroid Sc protrudes and variations in the height of spots in the opposite direction Hd of the direction Hu from the height of the surface of the throat St during breathing, which is a reference position, are separately added up. The method of separately adding up the height variations prevents the phenomenon that a height variation does not appear on the graph although the height variation exists actually.

Figure 10C:
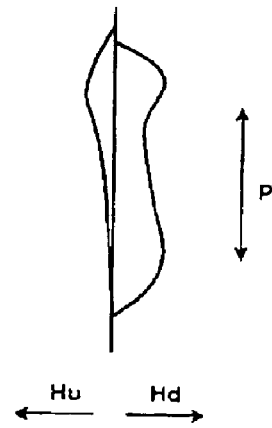

FIG. 10C is a graph illustrating the sum of height variations, as the distribution of height variations, when the height variations are separately added up in the direction Hu in which the thyroid Sc protrudes and in the opposite direction Hd of the direction Hu at the point of time corresponding to that shown in the graph of FIG. 10B. As can be seen from FIG. 10C, the height variation in the direction Hu in which the thyroid protrudes appears on the graph, which has hardly appeared on the graph shown in FIG. 10B. When it is determined whether the sum of height variations satisfies a predetermined condition on the basis of the graph shown in FIG. 10C, the predetermined condition corresponding to the sum of height variations is beforehand examined and is then stored in the swallowing function evaluating unit 22 (see FIG. 1), and the swallowing function of the examinee is evaluated on the basis of the analysis result referred to the swallowing function evaluating unit 22. The doctor, not the computer, may diagnose the swallowing disorder on the basis of the index. In this embodiment, the sum of height variations does not need to be graphed either.

In the third analysis example, only height variations in the direction Hu in which the thyroid Sc protrudes from the height of the surface of the throat St during breathing, which is a reference position, may be added up, and a position where the sum of height variations is the maximum value in the direction P in which the thyroid moves or a position (for example, a position Gu, which will be described later) indicating the bias of the sum of height variations in the direction P in which the thyroid moves may be regarded as the position of the thyroid Sc. Then, as in the first analysis example, the movement distance of the thyroid Sc may be calculated, and the movement distance of the thyroid may be used as an index for evaluating the swallowing function.

Analysis Example 4

Figure 11:
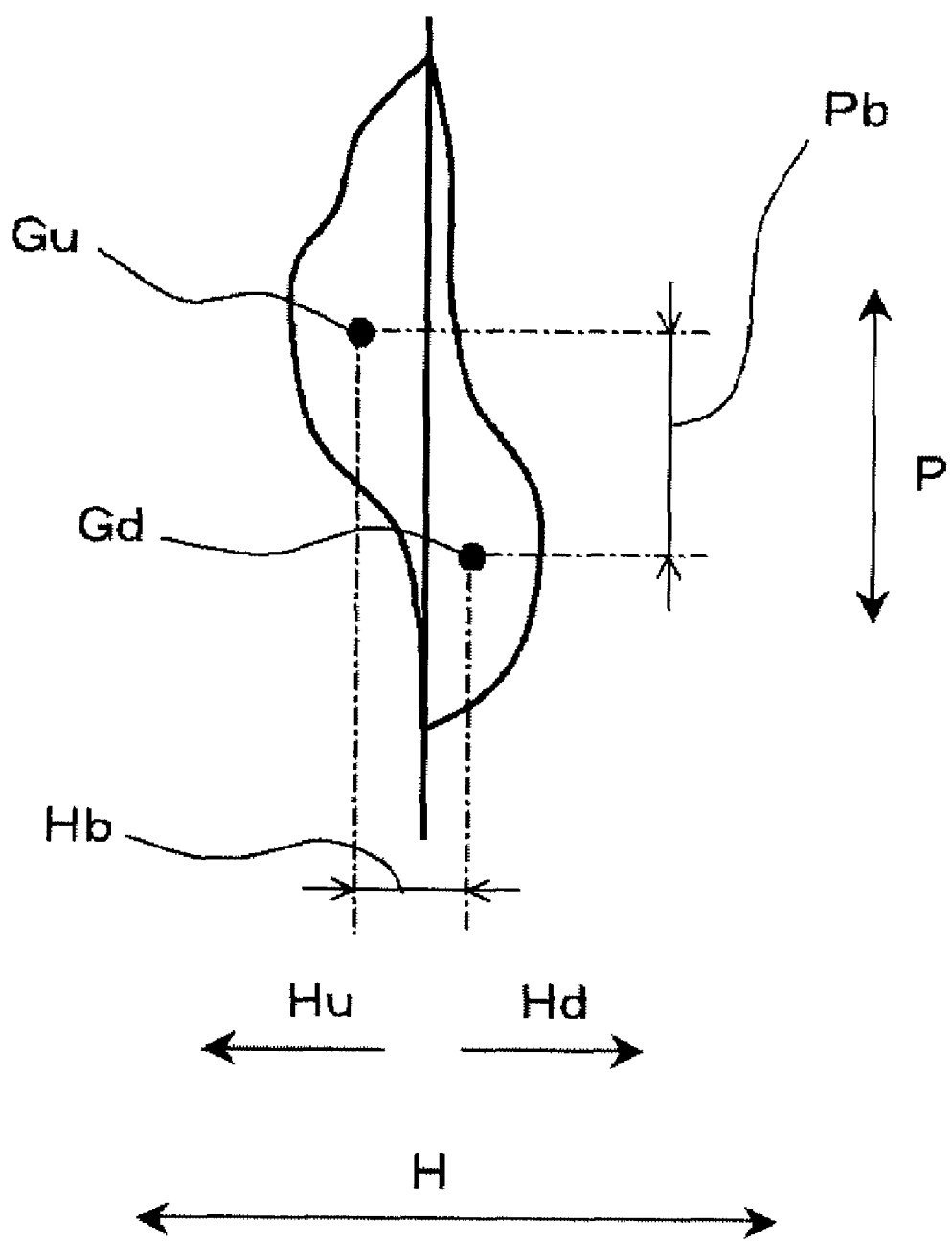
FIG. 11 is a diagram illustrating a height direction component deviation distance and a thyroid moving direction component deviation distance.

As shown in FIG. 11, in a fourth analysis example, variations in the height of spots from the fixed reference image are separately added up in the direction Hu in which the thyroid Sc protrudes and in the opposite direction Hd of the direction Hu, and a graph is made using the sums of height variations. Then, positions Gu and Gd indicating the bias of the distribution of each of the sums of height variations are calculated, and a height direction component deviation distance Hb, which is the distance in the height direction H between the two positions Gu and Gd, and a thyroid moving direction component deviation distance Pb, which is the distance in the direction P between the two positions Gu and Gd, are calculated. Here, the direction P is a direction in which the thyroid moves. In FIG. 11, the positions Gu and Gd indicating the bias are the central of gravity positions of the distributions, but they may be peak positions of the distributions (where the maximum value is obtained). When the positions Gu and Gd are put at the central of gravity positions of the distributions, the influence of noise is reduced. When the positions Gu and Gd are put at the peak positions of the distributions, the comparison with the threshold value becomes clear. Therefore, the calculated height direction component deviation distances Hb and thyroid moving direction component deviation distance Pb are used as values (indexes) for evaluating the swallowing function. Either one of the height direction component deviation distance Hb and the thyroid moving direction component deviation distance Pb may be calculated and then used as the evaluation value, or both of them may be calculated and then used as the evaluation values. It is estimated that the height direction component deviation distance Hb is correlated with a variation in the height direction H, and the thyroid moving direction component deviation distance Pb is correlated with the moving speed of the thyroid. In the fourth analysis example too, the swallowing function evaluating unit 22 may compare the evaluation value with a value for determining whether a person has the swallowing disorder, which has been stored therein beforehand, to evaluate the swallowing function, or the doctor, not the computer, may diagnose the swallowing disorder on the basis of the index. The positions Gu and Gd may be calculated by using numerical processing of the computer, not using the graph.

Analysis Example 5

In a fifth analysis example, the height direction component deviation distance Hb or the thyroid moving direction component deviation distance Pb is time-serially calculated for each of the captured frames, and the maximum value that is time-serially viewed is used as a value for evaluating the swallowing function. In this way, it is possible to narrow the objects of evaluation down and select the most remarkable value of the objects of evaluation and use the selected value as the object of evaluation. In this case, for reference, the height direction component deviation distance Hb or the thyroid moving direction component deviation distance Pb is time-serially obtained for each of the captured frames, and is then graphed. Then, it is possible to understand the tendency of the swallowing disorder from the appearance of the graph. In addition, both the maximum value of the height direction component deviation distance Hb and the maximum value of the thyroid moving direction component deviation distance Pb may be obtained and used both of them as evaluation values (indexes). Further, in a predetermined period (for example, typically period during the swallowing motion), the maximum value of the ratio of the variation of the height direction component deviation distance Hb to the maximum value thereof or the maximum value of the rate of change (gradient of change), and the maximum value of the ratio of the variation of the thyroid moving direction component deviation distance Pb to the maximum value thereof or the maximum value of the rate of change (gradient of change) may be used as evaluation values (indexes).

Figure 12:
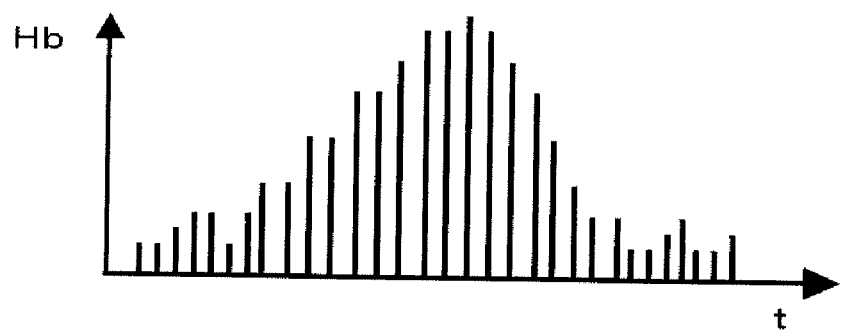
FIG. 12 is a graph time-serially illustrating the height direction component deviation distance.

FIG. 12 is a graph illustrating the height direction component deviation distance Hb that is time-serially obtained for each of the captured frames. In the graph shown in FIG. 12, the vertical axis indicates the height direction component deviation distance Hb, and the horizontal axis indicates time t. When a normal swallowing motion not having the swallowing disorder is performed and the thyroid is lifted up most, the height direction component deviation distance Hb becomes large. Then, when the swallowing motion is completed, the height direction component deviation distance Hb decreases. Therefore, a mountain-shaped graph is made as shown in FIG. 12. On the other hand, when the normal swallowing motion is not performed e.g. due to weak muscular strength and thus the thyroid is lifted up at a short distance, the height direction component deviation distance Hb becomes smaller in the overall period of the swallowing motion and the graph seems to be flatter than that in the graph shown in FIG. 12. When the swallowing function is evaluated, the maximum value of the gradient or the maximum value of the graph shown in FIG. 12 is preferably used as the evaluation value (index). The graph is made to visualize the swallowing function. Therefore, when the computer uses numerical contrast to evaluate the swallowing function, the graph may not be made. In the fifth analysis example, the swallowing function evaluating unit 22 may also compare the evaluation value with a value for determining whether a person has the swallowing disorder, which has been stored therein beforehand, to evaluate the swallowing function, or the doctor, not the computer, may diagnose the swallowing disorder on the basis of the index.

Analysis Example 6

In a sixth analysis example, variations in the height of spots from the fixed reference image are separately added up in the direction Hu (see FIG. 2) in which the thyroid Sc protrudes and in the opposite direction Hd (see FIG. 2) to the direction Hu, and the sums S1, S2, . . . , Sn of height variations are calculated for each of the captured frames. Then, the absolute values of the sums S1, S2, . . . , Sn of height variations are separately added up in the direction Hu (see FIG. 2) in which the thyroid Sc protrudes and in the opposite direction Hd (see FIG. 2) to the direction Hu to calculate the total sum TS (TS=|S1|+|S2|+ . . . |Sn|). Subsequently, the total sum TS is time-serially calculated for each frame and is used as a value (index) for evaluating the swallowing function.

Figure 13:
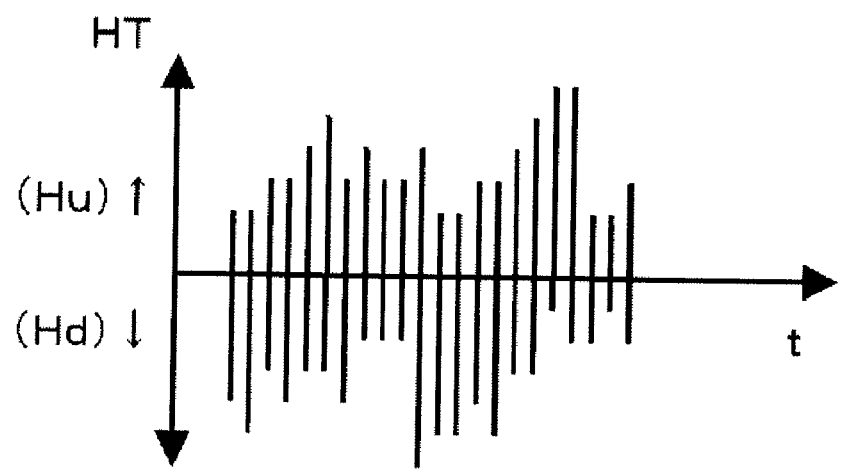
FIG. 13 is a graph time-serially illustrating the total sum.

FIG. 13 is a graph time-serially illustrating the total sum TS. In the graph shown in FIG. 13, the vertical axis indicates the total sums HT separately obtained in the direction Hu in which the thyroid Sc protrudes and in the opposite direction Hd to the direction Hu, and the horizontal axis indicates time t. The total sum TS is obtained by adding up the total sums HT separately obtained in the direction Hu in which the thyroid Sc protrudes and in the opposite direction Hd to the direction Hu. In FIG. 13, the whole length of each bar indicates the total sum TS. When the total sum TS or the total sums HT separately obtained in the directions Hu and Hd are used as values for evaluating the swallowing function, it is possible to evaluate the swallowing function on the basis of a variation in the position of the surface of the throat during the swallowing motion. In the sixth analysis example, the swallowing function evaluating unit 22 may also compare the evaluation value with the value for determining whether a person has the swallowing disorder, which has been stored therein beforehand, to evaluate the swallowing function, or the doctor, not the computer, may diagnose the swallowing disorder on the basis of the index.

(Visualization of Analysis Result)

Figure 14:
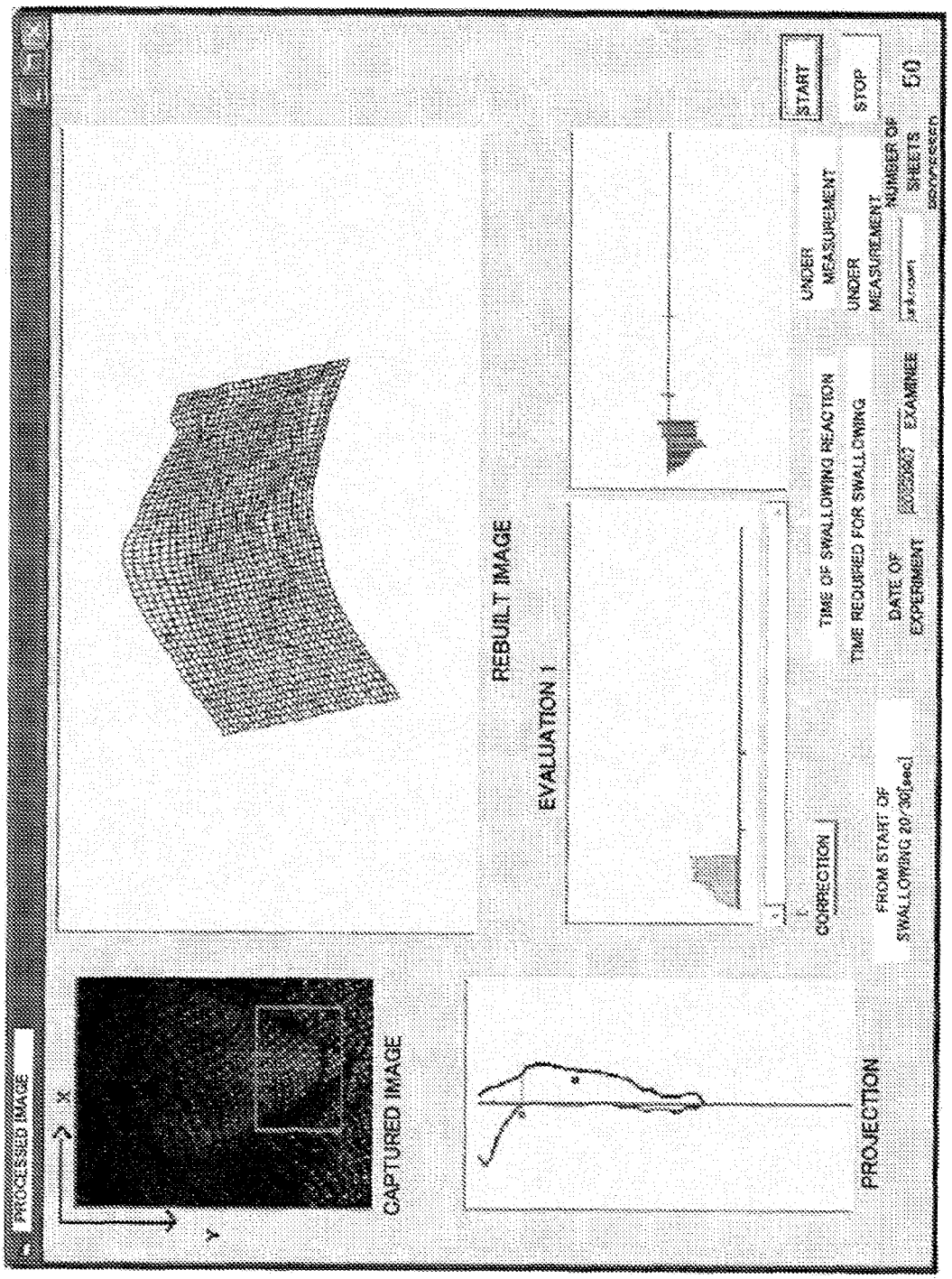
FIG. 14 is a diagram illustrating an example of a screen on which the analysis result is visually displayed.

FIG. 14 shows an example of the screen on which a height variation in the position of the surface of the throat St, the analysis result or the like is visually displayed. The screen shown in FIG. 14 is displayed by the display device 30 (see FIG. 1). The visualization of the height variation makes it possible to sensuously understand the quantitative evaluation of the swallowing function on the basis of the analysis result.

The image time-serially captured by the image capturing device 12 (see FIG. 1) of the FG sensor 10 may be stored in the image storage unit 23 (see FIG. 1) of the computer in real time, and the acquisition of the shift of the image of a bright spot, the position of the image of the bright spot or the above described analysis may be performed when the processing load of the computer is small. In this way, it is possible to obtain various types of analysis results without applying a heavy load to the computer. In addition, even when it is difficult to process the analysis within a 1/30 second because of the restriction of the calculation power of the computer, it is possible to calculate a height variation on the basis of the stored images. Further, when the evaluation result of the swallowing function is notified to the examinee together with the stored image, information on the position of bright spots, and analysis data, it is possible to make the examinee easily understand the evaluation of the swallowing function, which is suitable for needs for informed consent currently attracting attention.

In the first to sixth analysis examples, the height variation is a variation from a fixed reference position, but the invention is not limited thereto. For example, the height variation may be a variation from the immediately previous position that is detected at a predetermined time interval.

DESCRIPTION OF REFERENCE NUMERALS

1: SWALLOWING FUNCTION EVALUATING APPARATUS
10: FG SENSOR (HEIGHT VARIATION DETECTING UNIT)
11: PROJECTING DEVICE
12: IMAGE CAPTURING DEVICE
13: ARITHMETIC UNIT
21: ANALYZING UNIT
22: SWALLOWING FUNCTION EVALUATING UNIT
23: IMAGE STORAGE UNIT
30: DISPLAY UNIT
126f: IMAGE PLANE
B: WIDTHWISE DIRECTION
H: HEIGHT DIRECTION
P: THYROID MOVING DIRECTION
D: BRIGHT SPOT
Dt: IMAGE OF BRIGHT SPOT
Fs: CYLINDRICAL SURFACE
Sc: THYROID
St: THROAT
Hb: HEIGHT DIRECTION COMPONENT DEVIATION DISTANCE
Pb: THYROID MOVING DIRECTION COMPONENT DEVIATION DISTANCE
δ: MOVEMENT DISTANCE

What is claimed is:

1. A swallowing function evaluating apparatus comprising:
a height variation detecting unit configured to detect a variation in a height of a position of a surface of a throat, without exerting a force to the surface of the throat, in a height direction in which a thyroid protrudes; and
an analyzing unit configured to obtain an index for evaluating a swallowing function, based on the variation,
wherein the height variation detecting unit is configured to detect variations in a height at a plurality of points in a thyroid moving direction in which the thyroid moves during a swallowing motion and in a widthwise direction that is orthogonal to both the thyroid moving direction and the height direction,
wherein the plurality of points are arranged in a plurality of rows, each row being arranged along the widthwise direction,
wherein the analyzing unit is configured to:
add up the variations in the height of at least 4 points in each row of points respectively to obtain an added up value for each row, the plurality of rows being arranged with a predetermined interval in the thyroid moving direction on the surface of the thyroid;
obtain the index using the added up values, each of the added up values corresponding to a respective row of the plurality of rows:
separately add up the variations in height in a protruding direction in which the thyroid protrudes and in an opposite direction opposite to the protruding direction to obtain separately added up values;
obtain, for each of the protruding direction and the opposite direction, a distribution of the added up values in the thyroid moving direction when the separately added up values are viewed in the thyroid moving direction, and
obtain, as the index, at least one of a height direction component deviation distance in the height direction between positions, each of the positions indicating a bias of a respective distribution of the distributions of the protruding direction and the opposite direction, and a thyroid moving direction component deviation distance in the thyroid moving direction between the positions.

2. The swallowing function evaluating apparatus according to claim 1,
wherein the height variation detecting unit includes:
a projecting device configured to project a plurality of bright spots in a target region;
an image capturing device configured to capture an image of the target region having the plurality of bright spots projected therein; and
an arithmetic unit configured to calculate a variation on the basis of a shift distance of the image of the bright spot between two frames of images captured by the image capturing device at different time points from each other.

3. The swallowing function evaluating apparatus according to claim 1, further comprising:
a display device configured to visually display the obtained index, wherein the display device is configured to display the obtained index to be visually displayed, in a convex or concave shape with respect to a cylindrical surface as a tentative reference plane.

4. A swallowing function evaluating apparatus comprising:
a height variation detecting unit configured to detect a variation in a height of a position of a surface of a throat, without exerting a force to the surface of the throat, in a height direction in which a thyroid protrudes; and
an analyzing unit configured to obtain an index for evaluating a swallowing function, based on the variation,
wherein the height variation detecting unit is configured to detect variations in a height at a plurality of points in a thyroid moving direction in which the thyroid moves during a swallowing motion and in a widthwise direction that is orthogonal to both the thyroid moving direction and the height direction,
wherein the height variation detecting unit time-serially detects the variation;
wherein the plurality of points are arranged in a plurality of rows, each row being arranged along the widthwise direction,
wherein the analyzing unit is configured to:
add up the variations in the height of at least 4 points in each row of points respectively to obtain an added up value for each row, the plurality of rows being arranged with a predetermined interval in the thyroid moving direction on the surface of the thyroid, wherein the adding up of the variations is carried out at each time point of the time-serially detecting;
obtain the index using the added up values, each of the added up values corresponding to a respective row of the plurality of rows;
separately add up the variations in height in a protruding direction in which the thyroid protrudes and in an opposite direction opposite to the protruding direction to obtain separately added up values;
obtain, for each of the protruding direction and the opposite direction, a distribution of the added up values in the thyroid moving direction when the separately added up values are viewed in the thyroid moving direction, and
obtain at least one of a height direction component deviation distance in the height direction between positions, each of the positions indicating a bias of a respective of the distributions of the protruding direction and the opposite direction, and a thyroid moving direction component deviation distance in the thyroid moving direction between the positions; and
wherein the analyzing unit has a function of time-serially acquiring the obtained at least one of the height direction component deviation distance and the thyroid moving direction component deviation distance during the swallowing motion and determining one of (A), (B) or (C) below as the index;
(A) a maximum value of the time-serially acquired at least one of the height direction component deviation distance and the thyroid moving direction component deviation distance,
(B) a maximum value of ratios of variations of the time-serially acquired at least one of the height direction component deviation distance and the thyroid moving direction component deviation distance to a maximum value of the variations of the time-serially acquired at least one of the height direction component deviation distance and the thyroid moving direction component deviation distance, and
(C) a maximum value of rates of changes of the time-serially acquired at least one of the height direction component deviation distance and the thyroid moving direction component deviation distance to a maximum value of the variations of the time-serially acquired at least one of the height direction component deviation distance and the thyroid moving direction component deviation distance.

5. The swallowing function evaluating apparatus according to claim 4, further comprising:
a display device configured to visually display the obtained index,
wherein the display device is configured to display the obtained index to be visually displayed, in a convex or concave shape with respect to a cylindrical surface as a tentative reference plane.

6. The swallowing function evaluating apparatus according to claim 4,
wherein the height variation detecting unit includes:
a projecting device configured to project a plurality of bright spots in a target region;
an image capturing device configured to capture an image of the target region having the plurality of bright spots projected therein; and
an arithmetic unit configured to calculate a variation on the basis of a shift distance of the image of the bright spot between two frames of images captured by the image capturing device at different time points from each other.

7. A swallowing function evaluating apparatus comprising:
a height variation detecting unit configured to detect a variation in a height of a position of a surface of a throat, without exerting a force to the surface of the throat, in a height direction in which a thyroid protrudes; and
an analyzing unit configured to obtain an index for evaluating a swallowing function, based on the variation,
wherein the height variation detecting unit is configured to detect variations in a height at a plurality of points in a thyroid moving direction in which the thyroid moves during a swallowing motion and in a widthwise direction that is orthogonal to both the thyroid moving direction and the height direction,
wherein the plurality of points are arranged in a plurality of rows, each row being arranged along the widthwise direction,
wherein the analyzing unit is configured to:
add up the variations in the height of at least 4 points in each row of points respectively to obtain an added up value for each row, the plurality of rows being arranged with a predetermined interval in the thyroid moving direction on the surface of the thyroid; and
obtain the index using the added up values, each of the added up values corresponding to a respective row of the plurality of rows, and using a predetermined position as a position of the thyroid,
wherein the predetermined position is a position where the added up value is maximum in the thyroid moving direction among the added up values, or the predetermined position is a position indicating a bias of a distribution of the added up values in the thyroid moving direction.

8. The swallowing function evaluating apparatus according to claim 7,
wherein the height variation detecting unit time-serially detects the variation;
the adding up of the variations is carried out at each time point of the time-serially detecting;
the analyzing unit obtains a movement distance of the predetermined position of the thyroid as the index.

9. The swallowing function evaluating apparatus according to claim 8, further comprising:
  a display device configured to visually display the obtained index,
  wherein the display device is configured to display the obtained index to be visually displayed, in a convex or concave shape with respect to a cylindrical surface as a tentative reference plane.

10. The swallowing function evaluating, apparatus according to claim 8,
  wherein the height variation detecting unit includes:
  a projecting device configured to project a plurality of bright spots in a target region;
  an image capturing device configured to capture an image of the target region having the plurality of bright spots projected therein; and
  an arithmetic unit configured to calculate a variation on the basis of a shift distance of the image of the bright spot between two frames of images captured by the image capturing device at different time points from each other.

11. The swallowing function evaluating apparatus according to claim 7, further comprising:
  a display device configured to visually display the obtained index,
  wherein the display device is configured to display the obtained index to be visually displayed, in a convex or concave shape with respect to a cylindrical, surface as a tentative reference plane.

12. The swallowing function evaluating apparatus according to claim 7,
  wherein the height variation detecting unit includes:
  a projecting device configured to project a plurality of bright spots in a target region;
  an image capturing device configured to capture an image of the target region having the plurality of bright spots projected therein; and
  an arithmetic unit configured to calculate a variation on the basis of a shift distance of the image of the bright spot between two frames of images captured by the image capturing device at different time points from each other.

13. A swallowing function evaluating apparatus comprising:
  a height variation detecting unit configured to detect a variation in a height of a position of a surface of a throat, without exerting a force to the surface of the throat, in a height direction in which a thyroid protrudes; and
  an analyzing unit configured to obtain an index for evaluating a swallowing function, based on the variation,
  wherein the height variation detecting unit is configured to detect variations in a height at a plurality of points in a thyroid moving direction in which the thyroid moves during a swallowing motion and in a widthwise direction that is orthogonal to both the thyroid moving direction and the height direction,
  wherein the height variation detecting unit time-serially detects the variation;
  wherein the plurality of points are arranged in a plurality of rows, each row being arranged along the widthwise direction,
  wherein the analyzing unit is configured to:
    add up the variations in the height of at least 4 points in each row of points respectively to obtain an added up value for each row, the plurality of rows being arranged with a predetermined interval in the thyroid moving direction on the surface of the thyroid; and
    obtain the index using the added up values, each of the added up values corresponding to a respective row of the plurality of rows, wherein the adding up of the variations is carried out at each time point of the time-serially detecting;
  wherein the analyzing unit obtains one of (A), (B) or (C) below as the index;
  (A) a first maximum value of first time-serially obtained total sums obtained by the analyzing unit, wherein the analyzing unit is configured to add up the variations in a thyroid protruding direction in which the thyroid protrudes and further add up in the thyroid moving direction first sums obtained as a result of the adding up of the variations in the thyroid protruding direction to time-serially obtain the first time-serially obtained total sums, each of the first time-serially obtained total sums being the total sum at each time point of the time-serially detecting,
  (B) a second maximum value of second time-serially obtained total sums obtained by the analyzing unit, wherein the analyzing unit is configured to add up the variations in an opposite direction to the direction in which the thyroid protrudes and further add up in the thyroid moving direction second sums obtained as a result of the adding up of the variations to time-serially obtain the second time-serially obtained total sums, each of the second time-serially obtained total sums being the total sum at each time point of the time-serially detecting, and
  (C) a third maximum value of third time-serially obtained total sums obtained by the analyzing unit, wherein the analyzing unit is configured to add up the variations in a thyroid protruding direction in which the thyroid protrudes and in an opposite direction thereto, and to further add up in the thyroid moving direction, absolute values of the sums obtained as a result of the separate adding of the variations in the thyroid protruding direction to time-serially obtain the third time-serially obtained total sums, each of the third time-serially obtained total sums being the total sum at each time point of the time-serially detecting.

14. The swallowing function evaluating apparatus according to claim 13, further comprising:
  a display device configured to visually display the obtained index,
  wherein the display device is configured to display the obtained index to be visually displayed, in a convex or concave shape with respect to a cylindrical surface as a tentative reference plane.

15. The swallowing function evaluating apparatus according to claim 13,
  wherein the height variation detecting unit includes:
  a projecting device configured to project a plurality of bright spots in a target region;
  an image capturing device configured to capture an image of the target region having the plurality of bright spots projected therein; and
  an arithmetic unit configured to calculate a variation on the basis of a shift distance of the image of the bright spot between two frames of images captured by the image capturing device at different time points from each other.

* * * * *